United States Patent [19]

Abel

[11] Patent Number: 4,878,377
[45] Date of Patent: Nov. 7, 1989

[54] VISCOMETER APPARATUS AND METHOD

[75] Inventor: James C. Abel, Cedar Hill, Tex.

[73] Assignee: Atlantic Richfield Company, Los Angeles, Calif.

[21] Appl. No.: 255,003

[22] Filed: Oct. 7, 1988

[51] Int. Cl.⁴ .......................................... G01N 11/14
[52] U.S. Cl. ........................................................ 73/59
[58] Field of Search ..................................... 73/59, 60

[56] References Cited

U.S. PATENT DOCUMENTS

| | | | |
|---|---|---|---|
| 2,096,222 | 10/1937 | Bock | 73/59 |
| 2,457,247 | 12/1948 | Lawshe | 73/59 |
| 2,703,006 | 3/1955 | Savins | 73/59 |
| 2,992,651 | 7/1961 | Krofta | 73/59 X |
| 3,435,666 | 4/1969 | Fann | 73/59 X |
| 4,175,425 | 11/1979 | Brookfield | 73/59 |
| 4,299,118 | 11/1981 | Gau et al. | 73/59 |

FOREIGN PATENT DOCUMENTS 425083  9/1974  U.S.S.R. .................................. 73/59

Primary Examiner—Stewart J. Levy
Assistant Examiner—Joseph W. Roskos
Attorney, Agent, or Firm—Michael E. Martin

[57] ABSTRACT

A rotary viscometer includes a rotor member having plural helically staggered mixing blades disposed on the outer surface thereof for thoroughly mixing a quantity of fluid whose viscosity is being measuring during rotation of the rotor member. The viscometer has a relatively large annular space between the rotor member and a stationary bob member, and the viscosity of hydraulic fracturing fluids for earth formations, in particular, of a type which exhibit increased viscosity at elevated temperatures, is measured by an improved method using the viscometer.

6 Claims, 1 Drawing Sheet

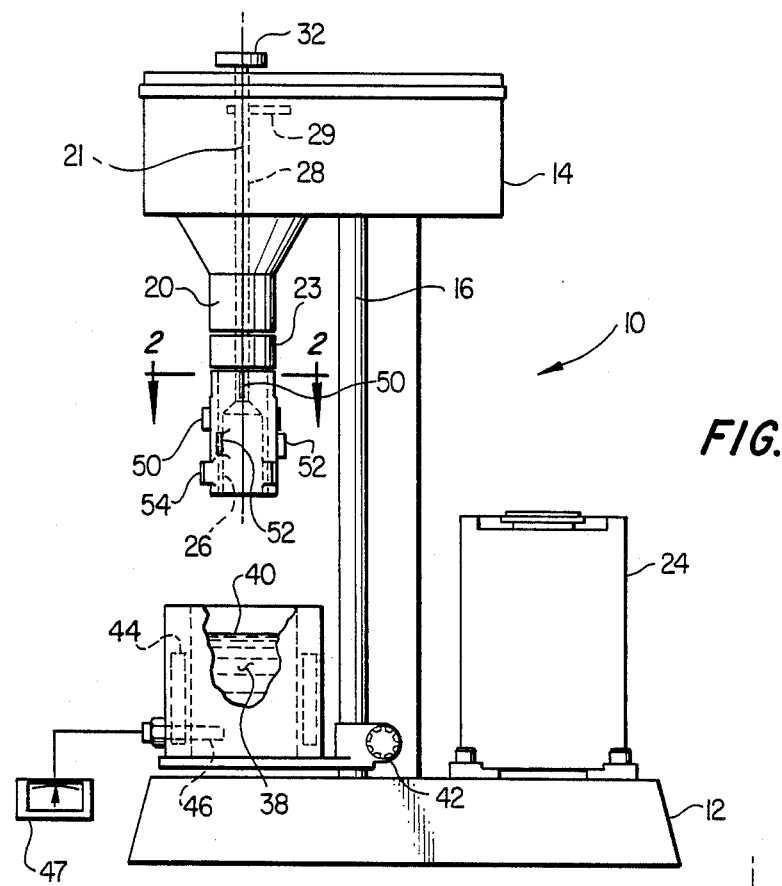
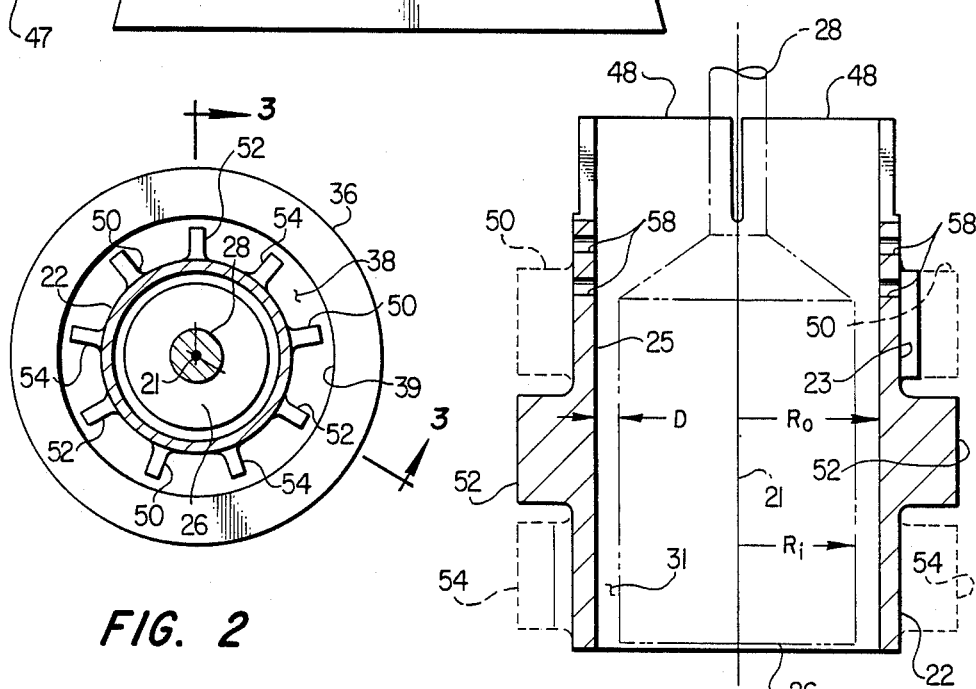
FIG. 1
FIG. 2
FIG. 3

VISCOMETER APPARATUS AND METHOD

FIELD OF THE INVENTION

The present invention pertains to a viscometer for measuring the apparent viscosity of relatively viscous fluids used in hydraulic fracturing of subterranean petroleum reservoirs wherein a modified viscometer rotor provides for uniform circulation and mixing of the fluid sample being analyzed. An improved method of field analysis of hydraulic fracturing fluids provides for measuring fluids which are subject to increased viscosity with increased temperature and time.

BACKGROUND

Fluids used in the hydraulic fracturing of petroleum reservoirs and other applications of viscous fluids often require field analysis of the apparent viscosity of the fluid as a quality control check and as a parameter useful in designing a fracturing operation or the like. One type of viscometer used in determining the apparent viscosity of a fluid is manufactured by NL Industries, Inc. under the trademark "Fann." This type of viscometer utilizes a tubular rotor which rotates about a stationary cylindrical bob member which is connected to a torsion spring for deflection under the viscous drag of the fluid which is disposed in an annular space between the rotor and the bob. Deflection measurements taken at different rotational speeds of the rotor corresponding to different shear rates yields information which may be converted to shear stress so that the fluid flow behavior indexes may be calculated and the apparent viscosity determined.

However, field analysis of relatively viscous liquids of the type which have a higher viscosity with increasing temperature, such as used in hydraulic fracturing operations, are somewhat unreliable using the conventional rotary viscometer. Accordingly, there has been a need for an improved type of viscometer which provides for thorough mixing of the fluid being heated for analysis and which is particularly adapted for field use at a well site for analyzing certain types of fluid samples. The present invention satisfies this need and provides and improved apparatus and method for making field viscosity measurements of fluids, particularly of the type used in hydraulic earth formation fracturing operations.

SUMMARY OF THE INVENTION

The present invention provides an improved viscometer apparatus of the rotary type wherein a sample of a fluid whose viscosity is to be measured is disposed in a container in which a rotor member rotates with respect to a stationary cylinder member or bob to measure the shear stress on fluid occupying the annular space between the rotor and the bob and wherein improved circulation and mixing of the fluid is provided by fluid mixing means disposed on the rotor member. In accordance with an important aspect of the present invention, a rotary viscometer rotor member is provided with a plurality of radially projecting circumferentially spaced mixing blades disposed on the outer circumference of the rotor member for mixing a quantity of fluid disposed in a cup or vessel and which includes means for changing the fluid temperature during the viscosity measurement process. The rotor mixing blades provide for the uniform distribution of heat through the fluid being measured and more accurate measurements of viscosity versus temperature and time, both critical factors in analyzing fluids used for hydraulic fracturing operations and certain other applications.

In accordance with another aspect of the invention, there is provided an improved method for measuring the apparent viscosity of a liquid, such as a hydraulic fracturing fluid, while the fluid is being heated to increase its temperature as a function of time by providing for thorough and uniform mixing of the fluid using the rotor of a rotary viscometer as the mixing device.

Those skilled in the art will recognize the above described aspects and superior features of the invention as well as other advantages thereof upon reading the detailed description which follows in conjunction with the drawing.

BRIEF DESCRIPTION OF THE DRAWING

FIG. 1 is a side elevation of an improved rotary viscometer in accordance with the present invention;

FIG. 2 is a section view taken generally along the line 2—2 of FIG. 1; and

FIG. 3 is a section view taken along the line 3—3 of FIG. 2.

DESCRIPTION OF A PREFERRED EMBODIMENT

In the description which follows like parts are marked throughout the specification and drawing with the same reference numerals, respectively. The drawing figures are not necessarily to scale and certain features of the apparatus illustrated may be shown in somewhat generalized or schematic form in the interest of clarity and conciseness.

Referring to FIG. 1, there is illustrated an improved viscometer apparatus generally designated by the numeral 10. The viscometer apparatus 10 is of a rotary type which has been modified in accordance with the present invention, but is basically available as a commercial unit under the trademark "Fann" from NL Industries, Inc., Houston, Texas. The viscometer 10 is characterized generally by a base member 12 which supports a rotor support head 14 on one or more upstanding column members 16. The support head 14 includes a rotary chuck 20 disposed thereon and adapted to rotate about an axis 21 and to drivingly engage and support a viscometer rotor member 22 in accordance with the present invention. A variable speed motor 24 is disposed on the base 12 and suitably drivingly engages the chuck 20 through drive mechanism, not shown. The head 14 also supports a stationary member commonly known as a bob 26 which is disposed concentrically within the tubular rotor member 22 and is connected to a support shaft 28 which is disposed for torsional deflection about the axis 21 against the bias of a spring 29, which deflection is measurable at a dial indicator 32 for determining the degree of deflection of the bob in response to viscous shear forces acting on the bob when the rotor 22 is rotating with a quantity of fluid disposed in the annular space formed between the rotor member 22 and the bob 26.

In the conventional version of the viscometer 10, the rotor member is a generally cylindrical tubular member having a collet upper end portion with a plurality of collet-like fingers which are gripped by the chuck 20 to keep the rotor member secured to the chuck, but the rotor member may be released by rotation of a collet nut 23 to permit release of the collet fingers by the chuck 20. The prior art counterpart of the rotor member 22 may be immersed in a quantity of liquid whose viscosity is to be measured whereby the liquid fills the annular space within the rotor member between the rotor member and the bob and rotation of the rotor member at a selected speed will provide for a measurement of the fluid viscosity by converting a reading taken at the indicator 32, which is commensurate with the torsional deflection of the bob 26, to a value of shear stress. The correlation between the shear rate which is related to selected speeds of rotation of the rotor member and the shear stress will provide a value of apparent viscosity which is useful in calculating pressure losses, flow rates and the progression of hydraulic fractures in earth formations.

In order to control the progress of a hydraulic fracture in an earth formation, it is desirable to provide fluid having a certain viscosity at the temperature of the formation itself. However, conventional hydraulic fluids, in order to have the desired viscosity at the elevated formation temperatures, would have viscosity so great at ambient temperatures at the earth's surface as to preclude efficient or effective pumping of the fluids. Accordingly, hydraulic fracturing fluids have been developed which include certain additives which accelerate or retard the change in viscosity in relation to the temperature so that the fluid may be efficiently and effectively handled at the surface, pumped down a wellbore without substantial pressure and flow losses and then have the proper viscosity while being pumped into the formation to extend the hydraulic fracture. Since it is desired to measure the effects of temperature and time on samples of the fluid as a means of quality control and analysis of the fracture process, it is necessary to heat fluid samples for measurement of their viscosity at the same temperature as expected to be encountered in the formation at the point of injection of the fluid. In this regard, the apparatus 10 is also provided with a container 36 having an interior chamber 38 in which a quantity of fluid 40 whose viscosity is to be measured is disposed. The container 36 is mounted on a support bracket 42 which is adapted to be supported by the column members 16 for movement to a position wherein the rotor 22 and bob 26 are immersed in the liquid 40 within the chamber 38. The container or cup 36 also includes a suitable heating element 44 for controlled heating of the liquid 40.

Referring now to FIGS. 2 and 3 also, the rotor 22 comprises a generally cylindrical tubular member having a tubular body part 23 which is formed to have a plurality of axially extending collet fingers 48 formed on one end thereof for insertion into the chuck 20 to be supported and rotatably driven by the chuck. The body part 23 has formed thereon a plurality of radially projecting and circumferentially spaced mixing blades 50, 52 and 54. Each of the blades 50 are essentially coplanar with each other with respect to a transverse plane through the axis 21 as indicated by the blades 50 which are shown in phantom in FIG. 3. In like manner, each of the blades 52 is coplanar with the other blades 52 in another transverse plane spaced axially from the plane of the blades 50, and each of the blades 54 is coplanar with the other blades 54 in a transverse plane spaced from the planes of the blades 50 and 52. Each set of blades 50, 52 and 54 are radially spaced apart and axially spaced apart to provide a helical cascade. A total of nine blades is illustrated for the rotor 22, and each blade is formed to extend substantially axially parallel to axis 21. The blades 50, 52 and 54 do not extend to the inner wall 39, FIG. 2, which delimits the chamber 38, but provide for thoroughly mixing the fluid 40 contained in the chamber as the rotor turns during a viscosity measuring process or in preparation for such a measurement to be taken. Accordingly, as the heating element 44 operates to heat the liquid sample 40 in the chamber 38, the liquid is thoroughly mixed to provide a uniform temperature of the liquid which is disposed in the annular space 29 between the bob 26 and the inner wall 25 of the tubular body part 23. Plural rows of circumferentially spaced and enlarged ports 58 are provided in the body part 23 adjacent to the upper row of mixing blades 50 to provide for improved circulation of liquid through the space 29 so that as the temperature of the liquid is changed by the heating element circulation of liquid into the space 29 is enhanced.

Typically, a hydraulic fracturing fluid having suitable thermally activated cross linking additives is heated over a predetermined time period while measuring the temperature and the apparent viscosity from reading the indicator 32 and performing certain calculations to arrive at a viscosity value. During the process of heating a fluid, such as the fluid 40, in the chamber 38, the rotor 22 is rotated while immersed in the fluid continuously at a selected constant speed while readings of a parameter by the dial indicator 32 corresponding to viscosity or shear stress are taken at predetermined intervals along with readings of temperature using a sensor 46 and its associated indicator 47. Tables 1 and 2 below show a comparison of the apparent viscosity at selected time intervals for an unmodified viscometer, that is a viscometer similar to the viscometer 10 but with a rotor 22 without the mixing blades 50, 52 and 54, respectively. The fluid measured to obtain the data for Tables 1 and 2 was a hydraulic fracturing fluid with thermally activated cross linking additives and known as Saturn Gel 50 made by Western Company of North America, Fort Worth, Texas.

TABLE 1

| Indicator Reading @ 300 RPM | Time (min.) | Temp. F. | Calculated Apparent Viscosity |
|---|---|---|---|
| 58 | 0 | 76 | 58 |
| 58 | .5 | 77 | 58 |
| 59 | 1.0 | 80 | 59 |
| 61 | 1.5 | 82 | 61 |
| 66 | 2.0 | 84 | 66 |
| 45–70 | 2.5 | 87 | |
| 40–65 | 3.0 | 89 | |
| 43–72 | 3.5 | 92 | |
| 47–77 | 4.0 | 95 | |

TABLE 2

| Indicator Reading @ 300 RPM | Time (min.) | Temp. F. | Calculated Apparent Viscosity |
|---|---|---|---|
| 28 | 0 | 76 | 58 |
| 28 | .5 | 78 | 58 |
| 32 | 1.0 | 80 | 66 |
| 36 | 1.5 | 81 | 76 |
| 42 | 2.0 | 83 | 97 |
| 44 | 2.5 | 85 | 104 |
| 48 | 3.0 | 88 | 121 |
| 52 | 3.5 | 91 | 135 |
| 68 | 4.0 | 94 | 186 |

As indicated by Table 1 at a predetermined viscosity increase, the apparent viscosity readings were unable to be taken above a temperature of 84 degrees F due to erratic readings from the indicator 32 which are used to calculate the apparent viscosity. However, when using the viscometer 10 modified to use the rotor 22 consistently uniform and steady readings were obtained at selected time intervals as indicated in the Table 2 for essentially the same temperature range as attempted for the readings taken in Table 1. The indicator readings, although different from the readings indicated in Table 1 were used to obtain viscosity by the equations indicated below. The equations were required because of a change in the width of the annular space 31 as measured by the radial dimension D in FIG. 3 which was increased in the modified viscometer according to the invention from 0.10 inches to 0.30 inches. The apparent viscosity, $\mu_{ap}$, of a power law fluid (in centipoises) may be expressed as $$\mu ap = \frac{47,800 \, K'}{\gamma 1 - N'} \quad (1)$$

where K' is the consistency index,
N' is the flow behavior index, and
$\gamma$ is the shear rate in sec$^{-1}$.

The conventional Fann viscometer is calibrated at 300 rpm rotor speed to read out the apparent viscosity directly. Correction factors allow operation at other speeds. Moreover, the flow behavior index, N' may be expressed:

$$N' = 3.32 \log\left(\frac{V_2}{V_1}\right) \quad (2)$$

where: $V_2$ is the viscometer apparent viscosity reading at a given rotor speed, i.e., 600 RPM and
$V_1$ is the apparent viscosity reading at one half the rotor speed of the $V_2$ reading, i.e., 300 RPM.

Moreover, the shear rate, $\gamma$, may be expressed as:

$$\gamma = \frac{2M\Omega}{1 - \left(\frac{R_i}{R_o}\right)2M} \quad (3)$$

$\Omega$ = rotor angular velocity in radians/sec.
M = 1/N'
$R_i$ = radius of the bob member 26 in centimeters
$R_o$ = inside radius of rotor member 22 in centimeters
The difference between these radii is the gap D, see FIG. 3.

Still further, the apparent viscosity, ap, may also, for the Fann viscometer, be expressed as:

$$\mu ap = \frac{K_1 K_2}{K_3} \cdot (100) \cdot \left(\frac{V}{n}\right) \quad (4)$$

where $K_1$ is the spring constant in dyne-cm for the bob member deflection spring,
$K_2$ is a constant dependent on the bob member 26 and comprises the volume in cubic centimeters of the bob member portion immersed in the fluid 40,
$K_3$ is the equivalent shear rate, $\gamma$, from equation (3) divided by the rotor speed n, V is the reading of the viscometer dial indicator 32 and
n is the viscometer rotor speed in RPM.

Accordingly, viscosities and the fluid indexes, K' and N', of relatively viscous fluids can be determined with the modified Fann viscometer or a similar rotary type viscometer by deriving the flow behavior index, N', for a particular fluid condition by taking viscometer readings at two different rotor speeds and calculating N' using equation (2). The shear rate for the same measurement conditions can be determined by substituting the value of N' in equation (3) along with the other values of the respective operating parameters. Calculation of the shear rate for the two different rotor speeds confirms the efficacy of the method by the close correlation of the values of shear rate obtained.

An average value of shear rate derived from calculations using equation (3) may be used. Since apparent viscosity can be calculated, once shear rate is known, from equation (4) for given viscometer conditions this value of viscosity can be used to determine the consistency index from equation (1) and with known values of the consistency index, K', and the flow behavior index, N', viscosity can be determined at any value of shear rate and can be used to determine pressure losses and flow characteristics in various situations.

The above example of taking a viscometer reading using a conventional fracturing fluid, such as the Saturn Gel 50, using the apparatus 10 and the method for determining the viscosity as set forth in the above noted equations provides a more accurate viscosity measurement to be taken with fluids which are subject to viscosity increase with increased temperatures, for example.

Although a preferred embodiment of a rotary viscometer in accordance with the present invention has been described in detail herein together with an improved method of determining viscosity of relatively viscous fluids using a modified rotary viscometer, those skilled in the art will recognize that various substitutions and modifications may be made to the specific embodiments disclosed without departing from the scope and spirit of the invention as recited in the appended claims.

What is claimed is:

1. A viscometer apparatus for measuring the viscosity of relatively viscous fluids such as thermally activated fracturing fluids for hydraulically fracturing earth formations, said apparatus comprising:
   a rotor member adapted to be driven at a selected speed, said rotor member including a generally tubular body part having an inner cylindrical wall of substantially constant radius;
   a stationary bob comprising a generally cylindrical part having an outer cylindrical surface of substantially constant radius and disposed in sleeved relationship within said rotor member to provide an annular space in which a quantity of fluid whose viscosity is to be measured is sheared at a predetermined rate by rotating the rotor member relative to the cylindrical part, said cylindrical part being connected to means for determining the torsional effort exerted on said bob;
   container means for containing a quantity of fluid to be tested, said container means being supported for placement of said rotor member and said bob in a chamber formed by said container means; and
   means on said rotor member comprising a plurality of mixing blades projecting radially outwardly from said body part with respect to the longitudinal central axis of said body part for mixing said fluid in said container means during rotation of said rotor member to provide uniform temperature distribution throughout said fluid in said container means during measurement of the viscosity of said fluid.

2. The apparatus set forth in claim 1 wherein:
said mixing blades are arranged spaced apart axially and circumferentially on said body part.

3. The apparatus set forth in claim 1 wherein:
said container means includes means for heating said quantity of fluid in said chamber during the measurement of viscosity of said fluid by said apparatus.

4. The apparatus set forth in claim 1 including:
plural rows of ports formed in said rotor member and opening into said annular space for circulating fluid between said annular space and said chamber.

5. A method for determining the viscosity of a relatively viscous fluid such as a thermally activated fracturing fluid comprising the steps of:
providing a rotary viscometer apparatus including a rotor member adapted to be driven at a selected speed, said rotor member including a generally tubular body part;
a stationary bob comprising a generally cylindrical part disposed in sleeved relationship within said rotor member to provide a relatively large annular space in which a quantity of fluid whose viscosity is to be measured is sheared at a predetermined rate by rotating the rotor member relative to said cylindrical part, said cylindrical part being connected to means for determining the torsional effort exerted on said bob, a container for containing a quantity of fluid to be tested and supported for placement of said rotor member and said bob in a chamber formed by said container, and means on said rotor member for mixing said fluid in said container during rotation of said rotor member to provide uniform temperature distribution throughout said fluid in said container during measurement of the viscosity of said fluid;

operating said rotor member at two selected speeds and determining the flow behavior index N' using the equation:

$$N' = 3.32 \log\left(\frac{V_2}{V_1}\right) \quad (2)$$

where $V_2$ and $V_1$ are indicative of the torsional effort on said bob at said two speeds, respectively;
determining the shear rate, $\gamma$, at least at a selected one of said two speeds of said rotor member from the equation:

$$\gamma = \frac{2M\Omega}{1 - \left(\frac{R_i}{R_o}\right)2M} \quad (3)$$

where $\Omega$ is the rotor speed in radians/sec., $M = 1/N'$, $R_i$ is the radius of said bob and $R_o$ is the radius of the inside wall of said rotor member; and
determining viscosity, $\mu ap$, of said fluid in said chamber from the equation $$\mu ap = \frac{K_1 K_2}{K_3} \cdot (100) \cdot \left(\frac{V}{n}\right) \quad (4)$$

where;
$K_1$ is a spring constant related to torsional bias on said bob, $K_2$ is a constant comprising the volume of said bob immersed in said fluid, and
$K_3$ is the shear rate divided by rotor speed in rpm, n is rotor speed in rpm, and V is a value read from said viscometer indicative of the torsional effort on said bob at rotor speed n.

6. The method set forth in claim 5 including the steps of:
determining the consistency index K' for said fluid from the equation $$\mu ap = \frac{47,800 \, K'}{\gamma 1 - N'} \quad (1)$$

using the values of viscosity, $\mu ap$, shear rate, $\gamma$, and the flow behavior index N' determined from equations (4), (3) and (2), respectively.

* * * * *